United States Patent [19]

McGowan, deceased et al.

[11] 3,988,094

[45] Oct. 26, 1976

[54] DENTAL FLASK

[76] Inventors: George F. McGowan, deceased, late of Kansas City, Mo.; by Jennie E. McGowan, heir, 4509 Forest, Kansas City, Mo. 64110

[22] Filed: Feb. 24, 1975

[21] Appl. No.: 552,710

[52] U.S. Cl. .............................. 425/175; 425/180; 24/263 A
[51] Int. Cl.² ...................... B28B 7/10; A44B 21/00
[58] Field of Search .............. 425/175, 179, 180, 2; 249/54, 66 R, 67, 68, 168, 146; 164/376; 151/38; 85/4; 292/256.73; 24/263 A; 32/2, 17

[56] References Cited
UNITED STATES PATENTS

| | | | |
|---|---|---|---|
| 1,331,193 | 2/1920 | Greenberg | 425/179 |
| 1,347,205 | 7/1920 | Brown | 425/180 |
| 1,875,660 | 9/1932 | Rodin | 425/178 |
| 1,926,508 | 9/1933 | Ballard | 425/179 |
| 2,420,545 | 5/1947 | Leader | 425/179 |
| 2,440,910 | 5/1948 | Opotow | 425/180 |
| 2,899,707 | 8/1959 | McGowan | 164/376 X |
| 2,903,062 | 9/1959 | Lambert | 249/146 X |
| 2,975,479 | 3/1961 | McGowan | 425/180 |
| 3,635,630 | 1/1972 | Greene | 425/175 |

Primary Examiner—Francis S. Husar
Assistant Examiner—John S. Brown
Attorney, Agent, or Firm—Schmidt, Johnson, Hovey & Williams

[57] ABSTRACT

A multi-section dental flask for denture-making is provided which includes a pair of threaded, longitudinally shiftable pins received in stepped, communicating bores in the anterior region of the primary and closure sections of the flask to permit selective movement of the pins between a position precluding significant relative movement of the flask sections and a position permitting limited degrees of such movement. The pins are shifted to their movement-blocking positions during all preliminary operations of the denture-making process, and thereafter moved to their recessed positions in order to ensure accurate reproduction of the denture model by compensating for the characteristic expansion and contraction of the denture material during hardening thereof. In another embodiment, a flask lid is utilized in conjunction with compression bolts for resiliently holding the resultant three-piece flask together during the curing process without the need for a separate spring compress as has heretofore been required. The flask lid preferably includes a releasably secured metallic ejector block which facilitates dislodgment of the finished denture from the hardened investment material within the flask.

3 Claims, 13 Drawing Figures

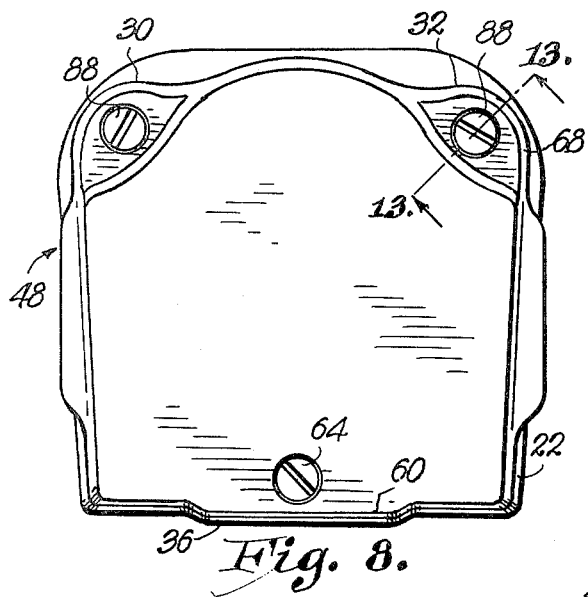
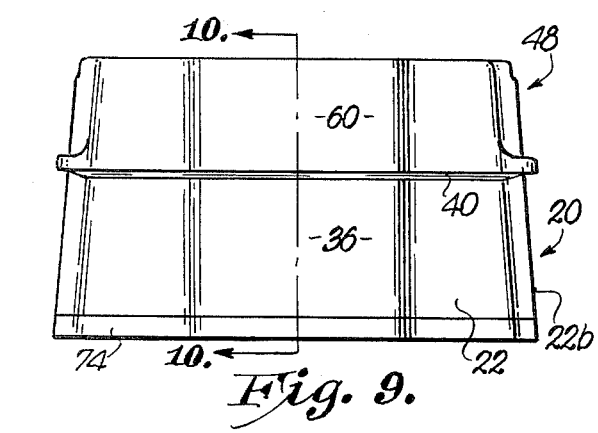
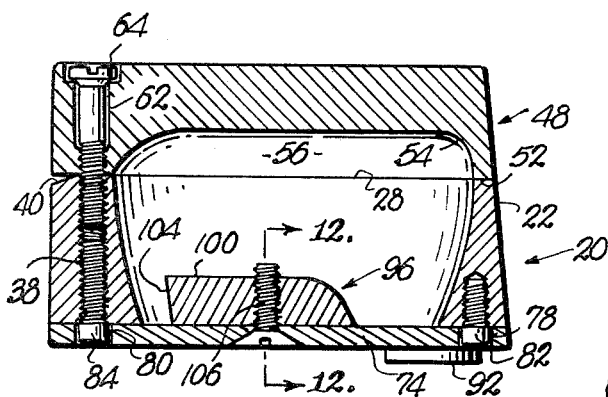
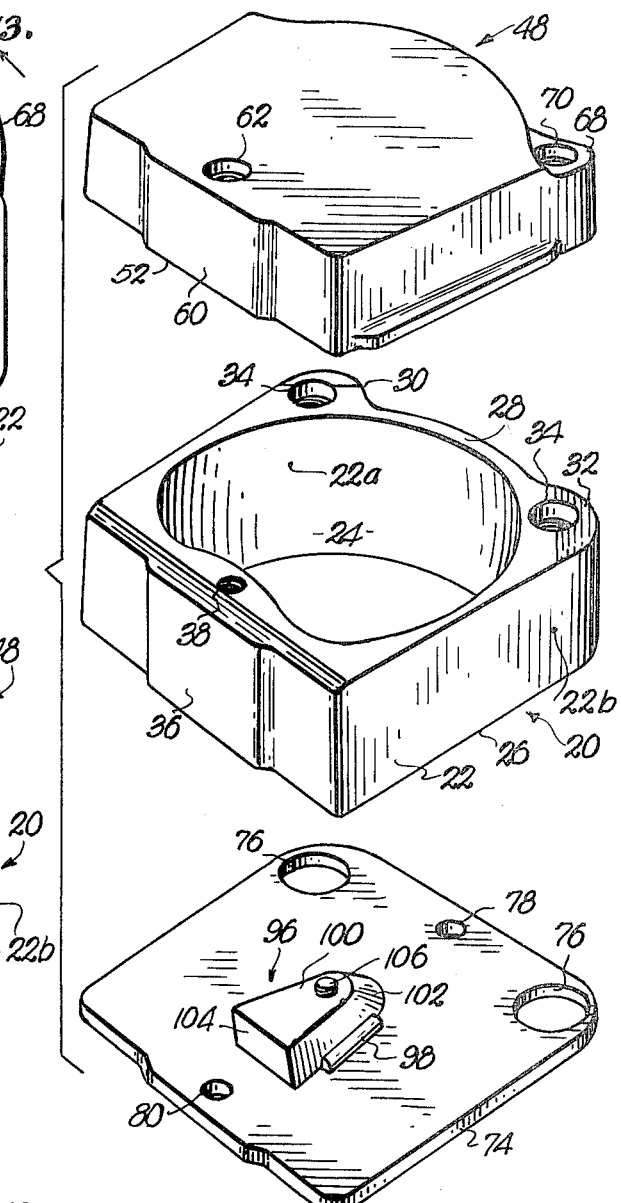
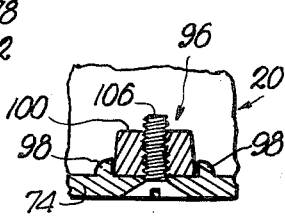
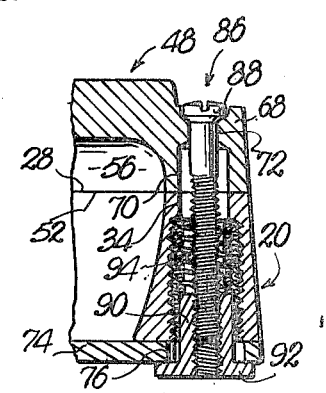

3,988,094

DENTAL FLASK

This invention relates to improvements in dental flasks used in the manufacture of dental devices such as dentures or the like. Steps of the various techniques of prosthetic dentistry are well known to those skilled in the art and are outlined in my U.S. Pat. Nos. 2,899,707, 2,975,479, and 3,772,792; accordingly, such techniques will not hereinafter be described in detail, but only as necessary to facilitate a complete understanding of the present invention.

While the dental flasks disclosed in the above patents have proven to be highly satisfactory in use, certain improved features are presented by the flask of the present invention which contributes substantially to attainment of the goal of providing a dental flask which assures the manufacture of a well-fitting dental device of high quality conforming accurately to the positive model upon which the device is based. The present invention is particularly concerned with providing structure for ensuring that the anterior region of the dental device is accurately reproduced from the positive model in order to minimize the possibility of producing a denture having an objectionable "open bite". In addition, another embodiment allows denture-making without the use of a conventional spring-biased dental compress, as has heretofore been required.

One important object of the instant invention is to provide a means for accurately aligning the separate sections of a dental flask and controlling the expansion of the denture material in both the molar and anterior tooth regions of the flask, thus avoiding the unsatisfactory situation wherein the respective tooth regions of the finished denture, while having been very carefully prepared with close adherence to the positive denture model, nonetheless are only inaccurate reproductions because of misalignment of the flask sections or unregulated expansion and contraction of the denture material therein.

Another important object of the present invention is to provide a dental flask having shiftable connective pin means operable to ensure accurate positioning of the separate flask sections during all preliminary denture-making operations, notwithstanding the fact that the pins can be moved to a recessed position permitting limited degrees of relative movement in order to compensate for the characteristic expansion and contraction of the polymeric denture material during final hardening thereof.

Another important aim of the invention is to provide a three-piece dental flask utilizing spring-loaded connective assemblies in the anterior region thereof in order to permit hardening of the denture material within the flask without the need of a dental compress or the like to hold the flask sections together as a single unit during curing.

A still further important object of the invention is to provide a selectively releasable ejector block on the lid section of a three-piece dental flask which is operable to be partially released and used as a means of facilitating removal of the completed denture from the hardened investment material within the flask.

In the drawings:

FIG. 8 is a top plan view of a three-piece dental flask in accordance with the invention;

FIG. 9 is an end elevational view of the three-piece flask;

FIG. 10 is a vertical sectional view taken along line 10—10 of FIG. 9;

FIG. 11 is an exploded perspective view depicting the three sections of the dental flask;

FIG. 12 is a fragmentary, vertical sectional view taken along line 12—12 of FIG. 10; and FIG. 13 is a fragmentary, vertical sectional view taken along line 13—13 of FIG. 8.

Figure 5:
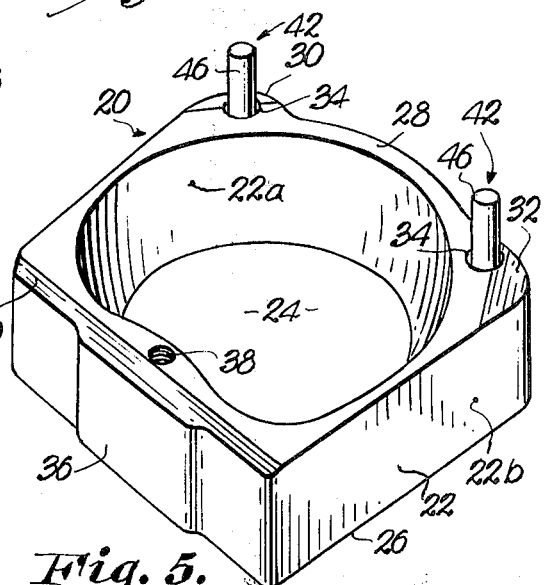
FIG. 5 is a perspective view of the tubular primary section of the flask depicted in FIGS. 1–3.

The improved dental flask includes a substantially tubular primary section 20 (FIG. 5) having a continuous sidewall 22 defining a central chamber 24, and a pair of open, opposed, lower and upper ends 26 and 28 respectively. Sidewall 22 is of generally pyramidal configuration, top to bottom, presenting an inwardly sloping inner surface 22a and an outwardly sloping outer surface 22b. A pair of forward, beveled ear portions 30 and 32 are formed at the adjacent front corners of sidewall 22 and each such ear portion is provided with an elongated, axially aligned threaded bore 34 therein which extends completely through primary section 20. A rectangular block 36 at the rearmost or molar portion of section 20 projects outwardly from sidewall 22 and provides an additional area at the top of sidewall 22 for a threaded bore 38. A bevel 40, beginning at bore 38 and extending across the full width of the back of section 20, slopes downwardly away from the top of sidewall 22 and chamber 24 until the outer surface 22b is reached.

An axially shiftable pin member 42 is received within each anterior bore 34 and includes a lower threaded section 44 (FIGS. 6 and 7) within the threaded section of the respective bores 34, with an integral, shaft-like extension 46 of reduced diameter extending therefrom and above the upper end 28 of section 20.

Figure 1:
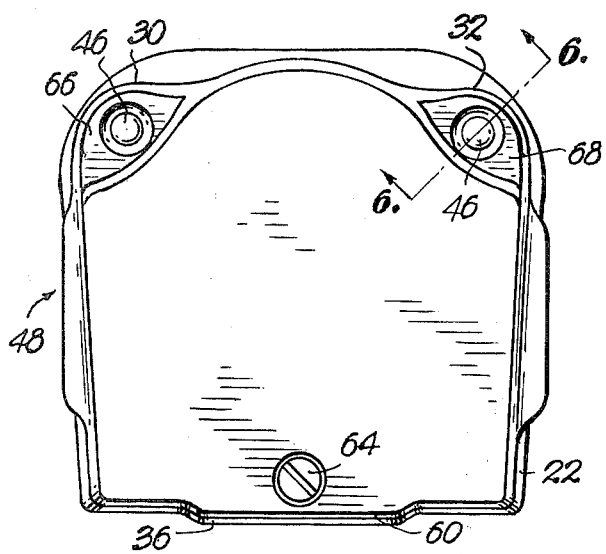
FIG. 1 is a top plan view of a two-piece dental flask in accordance with the invention.
Figure 4:
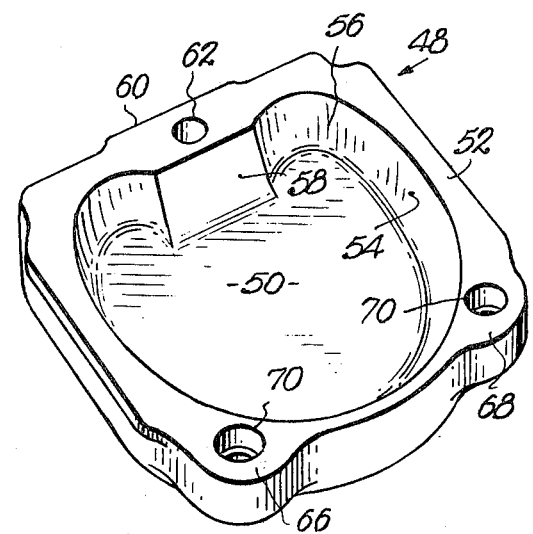
FIG. 4 is a perspective view of the closure section of the flask illustrated in FIGS. 1–3, shown in an inverted position to illustrate the construction thereof.
Figure 2:
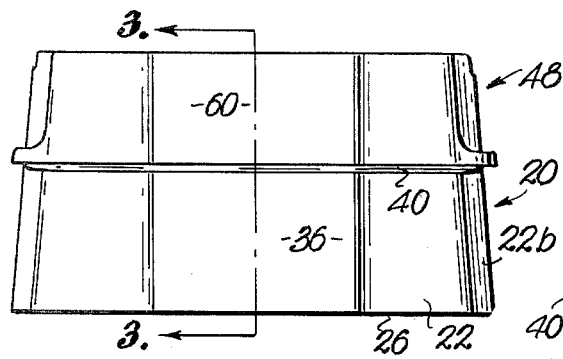
FIG. 2 is an end elevational view of the flask.
Figure 3:
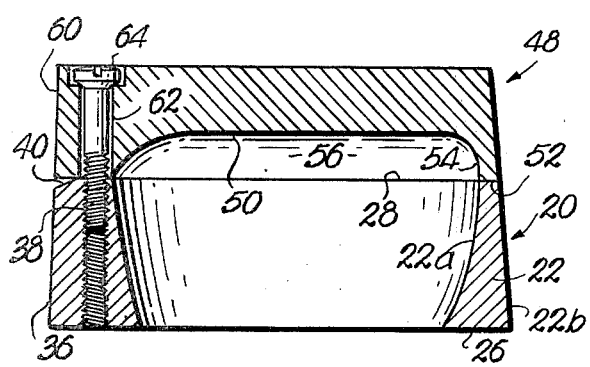
FIG. 3 is a vertical sectional view taken along line 3—3 of FIG. 2.

The flask further includes a closure section 38 adapted to cover end 28 of section 20 as illustrated in FIGS. 1–3. Section 48 has a recessed inner face 50 provided with a peripheral edge 52 and a continuous, sloping sidewall 54 to define a cavity 56 within the section. An arcuate, ramp-like pad 58 is strategically located in cavity 56 at the back of the latter and presents a smooth, inclined surface. A block 60, similar to block 36 of section 20, is integral with the back of closure section 48 and has a smooth, counterbored hole 62 disposed proximal thereto completely through section 48 for alignment with threaded bore 38 in section 20 when the flask is assembled. A conventional bolt 64 is received by bore 62 and threadably received by bore 38 for the purpose of releasably holding the sections 20 and 48 together.

Figure 6:
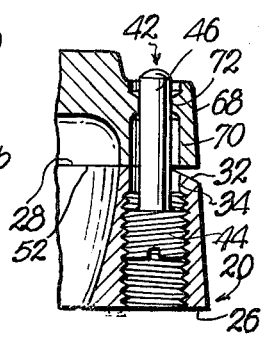
FIG. 6 is a fragmentary, vertical sectional view taken along line 6—6 of FIG. 1 and illustrating the shiftable connective pin means in its uppermost, movement-blocking disposition.
Figure 7:
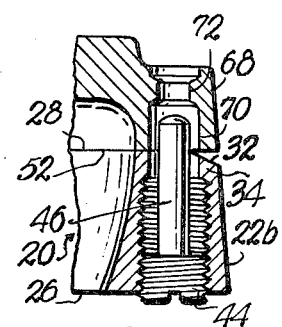
FIG. 7 is a view identical with that of FIG. 6, showing the pin means in its lowermost, retracted position.

Closure section 48 also includes a pair of protruding ear segments 66 and 68 at the forward or anterior region thereof. Each ear section is provided with a stepped, axially aligned bore 70 therethrough which is configured and arranged to register with a corresponding bore 34 in primary section 20. Referring specifically to FIGS. 6 and 7, it will be seen that each bore 70 includes a lowermost section of diameter substantially equal to that of bore 34, with a section 72 of restricted diameter slightly below the top of bore 70. Section 72 is substantially equal in diameter to the shaft-like extension 46 of pin members 42, such that when the latter are moved to the movement-blocking positions thereof illustrated in FIG. 6, significant relative movement between sections 20 and 48 is effectively precluded.

Referring now to FIGS. 8–13, a second embodiment of the present invention will be described. In this instance, identical primary enclosure sections 20 and 48 respectively are employed, but a third lid section 74 is also utilized to cover the lower end of primary section 20. Lid section 74 is a generally planar member, including a pair of relatively large forward apertures 76 configured and arranged to align with the corresponding bores 34 in primary section 20. A relatively small bore 78 is provided between the bores 76 proximal to the forward marginal edge of lid section 74, with a similar bore 80 being provided adjacent the rearmost central part of the latter. A pair of threadably secured studs 82 and 84 project from the lowermost end 26 of primary section 20 and are received within corresponding bores 78 and 80 for the purpose of locating and properly orienting lid section 74 (FIG. 10).

When lid section 74 is utilized in conjunction with sections 20 and 48, it is possible to employ a pair of compression bolt assemblies 86 which extend through the three sections and resiliently hold the same together in order to permit curing of polymeric denture material within the flask without the need of a separate spring compress or the like. Each compression bolt assembly 86 includes an elongated bolt 88 which extends through a stepped bore 70 in closure section 48 and into a corresponding bore 34 within primary section 20. An internally threaded, annular sleeve member 90 is positioned within the lowermost end of each bore 34 which receives the threaded end of a bolt 88. In this regard, each sleeve member 90 includes a lowermost radial flange 92 which abuts the surface of lid section 74 remote from primary section 20 in order to hold section 74 in its proper position. Finally, a helical spring 94 is situated within the threaded portion of each bore 34 in engagement with the end of sleeve member 90 and the uppermost annular edge of the threaded section of bore 34, respectively.

In preferred embodiments, lid section 74 includes a central, releasable ejector block 96 formed of heat conductive metallic material. Block 96 is positioned between a pair of spaced guides 98 integral with the inner face of lid section 74, and presents a generally smooth upper face 100 and a continuous, sloping sidewall 102. As best illustrated in FIG. 10, the rearward face 104 of block 96 is tapered inwardly from top 100 in order to create an undercut region between the latter and the inner face of lid section 74. A conventional flat-head screw 106 extends through complementary bores in lid section 74 and block 96 for the purpose of releasably holding the latter in position between guides 98.

In use, the steps in preparation of a denture as outlined in my U.S. Pat. Nos. 2,899,707; 2,975,479; and 3,772,792 are easily and most effectively carried out. In particular, before commencing initial operation with the flask assembly, pin members 42 are moved upwardly within their associated bores 34 to a point where the shaft-like extensions 46 thereof extend into complemental, connective disposition with the restricted diameter section 72 within bores 70. At this point the preliminary operations in the denture-making procedure can be carried out without fear that the primary enclosure sections 20 and 48 will become misaligned during requisite successive separations and closures thereof. This objectionable result is, of course, positively precluded by the close fit between shaft-like extensions 46 and portion 72 of the bores 70 in closure section 48. After a pattern has been formed for the denture within investment material disposed in primary section 20 and closure section 48, the artificial teeth which have been previously mounted upon a wax base remain embedded within the investment material of section 20 when the latter and section 48 are separated. Thereupon, the wax within primary section 20 is removed and a suitable polymeric substance is deposited within the pattern previously formed by the removed wax base, and the sections 20 and 48 are reassembled and properly oriented by means of the shiftable pin members 42 as described. At this point, the two sections are subjected to a trial press and any excess polymeric material is removed. Thereupon, the flask assembly is "finally closed" and the retractable pin members 42 are moved to the recessed dispositions thereof as illustrated in FIG. 7. The sections 20 and 48 can now optionally be placed between the opposed jaws of a suitable curing compress, such as the type disclosed in my U.S. Pat. Nos. 3,267,525; 3,411,184; and 3,571,858.

As the polymeric substance cures within the confines of the solidified investment material within the flask, the substance seeks to expand; in this respect, because of the fact that the polymeric substance characteristically must expand and contract during the curing process, it follows that different regions of the flask may be subjected to differing pressures during such process. The flask of the present invention is particularly adapted to accommodate such variable expansion forces by the provision of the novel pin means described for assuring freedom of movement between the respective flask sections.

For example, when the pin members 42 are moved to their retracted positions, the expanded diameter sections of the corresponding bores 70 permit limited degrees of movement transversely of the pins, as well as vertically thereof. Moreover, during such movement the rearward bolt 64 and bevel 40 on section 20 come into play. As the polymeric substance within the flask seeks to expand against the spring compress holding the latter, closure section 48 will begin to fulcrum about an axis passing through bolt 64 with the junction of bevel 40 with the top of upper end 28 defining the fulcrum and its axis. Because the fulcrum point for section 48 is disposed rearwardly of the molar region of the flask, the front or anterior section thereof is permitted to raise more than the back, effecting a like amount of restraint on the polymeric substance, since substantially more of this substance is required for the molar region of the denture than the anterior region thereof. Therefore, when the polymeric substance is cooled, after expanding, it contracts to a position wherein the molar region of the denture is not disproportionately larger than the anterior region, at variance with the accurately and carefully prepared pattern for the denture.

After the polymeric substance has cured, the flask is disassembled and the investment material within cavity 56 of section 48 removed. During separation of the two sections 20 and 48, it will be appreciated that a suitable tool such as a screwdriver may be inserted between the sections to aid in prying the flask apart.

After the investment material has been removed from cavity 56, the flask can again be reassembled and placed with an ejector device between the opposed jaws of a curing compress in order to effect removal of the investment material and denture within primary section 20, all as disclosed in my prior U.S. Pat. No. 3,772,792.

In alternative procedures particularly utilizing the embodiment of the invention disclosed in FIGS. 8–13, a threepiece flask having unique compression assemblies is employed which completely eliminates the need for a separate spring compress or the like. In particular, the denture-making procedure proceeds exactly as described with the pin members 42 in their extended, movement-blocking dispositions to preclude relative shifting of sections 20 and 48. However, upon the initial packing of primary section 20 with investment material during the procedure, lid 74 is placed over the open end 26 of section 20 and properly oriented by means of studs 82. By virtue of the undercut backwall 104 of ejector block 96 secured to lid section 74, the latter is securely held in place by the hardened investment material during all subsequent operations. Thus, the denture-making procedure can continue with no difficulty because of lid section 74. However, when the flask sections 20 and 48 are "finally closed" as described above, the respective pin members 42 can be completely removed from bores 34 within primary section 20, and the compression bolt assemblies 86 substituted therefor. In this regard, the elongated bolts 88 are first positioned within the mated bores in the primary and closure sections, whereupon coil spring 94 and internally threaded sleeve 90 are installed as depicted in FIG. 13. Bolts 88 are then tightened to substantially compress spring 94 and draw the radial flanges 92 of sleeve members 90 against the underside of lid section 74. When completely tightened down, it will be appreciated that substantially no movement is permitted between the three flask sections 20, 48 and 74. In order to permit such necessary movement, the bolts 88 are each turned back an appropriate amount (for example, one quarter of a turn) in order to permit limited degrees of movement between sections 48 and 20, which in turn accommodates the characteristic expansion and contraction of the polymeric denture material within the flask. It will also be seen that the springs 94 engaging the corresponding sleeves 90 serve to resiliently urge the primary and closure sections together for ensuring a closely fitting contact therebetween.

It will also be recognized that the three-piece flask depicted in FIGS. 8–13 completely eliminates the need for a separate spring compress in the curing process. Thus, a single flask unit can be processed individually as opposed to the prior compresses which conventionally are constructed to accommodate two stacked flasks during the curing process.

Another important feature of this embodiment resides in the function of ejector block 96. In particular, when it is desired to remove the cured denture from the flask, it is only necessary to loosen flat-head bolt 106 so as to extend its head above the surface of lid section 74. The bolt-head can then be struck against a flat surface which has the effect of shifting block 96 and facilitating dislodgment of the finished denture and investment material to allow the easy removal thereof. Finally, by virtue of the heat conductive nature of block 96, it serves as a "thermo-duct" which hastens the hardening of the investment and polymeric denture materials within the flask during denture-making procedures.

Having thus described the invention, what is claimed as new and desired to be secured by Letters Patent is:

1. A dental flask comprising:
   a substantially tubular primary section having opposed open ends;
   a closure section disposed in covering relationship to one of said open ends;
   a lid positioned in covering relationship to the other of said open ends,
   said primary section, closure section and lid being cooperatively configured to define at least a pair of spaced, axial bores extending through the lid, the tubular wall defining said primary section, and said closure section;
   an elongated internally threaded tubular sleeve removably positioned within each of said bores and having a radial flange in engagement with the face of said lid remote from said primary section;
   elongated, threaded bolt means positioned within each of said axial bores with the threaded end thereof received within the corresponding sleeve, the disposition of said bolt means serving to draw said closure section, primary section and lid together;
   spring means positioned about each of said bolt means and engaging the corresponding sleeve for resiliently urging the closure section into closely fitting contact with said primary section.

2. The dental flask of claim 1 wherein a pair of said primary section bores are positioned in the forward marginal edge of said primary section, the rearward edge of the latter remote from said primary bores being beveled to present a fulcrum for said closure section, there being elongated connector means extending through said sections and intersecting said beveled edge.

3. The dental flask of claim 1 wherein said lid includes a heat conductive ejector block releasably positioned on the face of said lid adjacent said primary section.

* * * * *